United States Patent [19]
McEwan

[11] Patent Number: 5,581,256
[45] Date of Patent: Dec. 3, 1996

[54] RANGE GATED STRIP PROXIMITY SENSOR

[75] Inventor: Thomas E. McEwan, Livermore, Calif.

[73] Assignee: The Regents of the University of California, Oakland, Calif.

[21] Appl. No.: 486,082

[22] Filed: Jun. 6, 1995

Related U.S. Application Data

[63] Continuation-in-part of Ser. No. 300,769, Sep. 6, 1994, Pat. No. 5,521,600.

[51] Int. Cl.$^6$ .................................................. G01S 13/04
[52] U.S. Cl. ............................................................ 342/27
[58] Field of Search .......................... 342/27, 28; 324/642

[56] References Cited

U.S. PATENT DOCUMENTS 4,328,487  5/1982  Cheal ........................................ 342/28
5,457,394  10/1995  McEwan .................................... 342/27

Primary Examiner—Daniel T. Pihulic
Attorney, Agent, or Firm—Henry P. Sartorio

[57] ABSTRACT

A range gated strip proximity sensor uses one set of sensor electronics and a distributed antenna or strip which extends along the perimeter to be sensed. A micro-power RF transmitter is coupled to the first end of the strip and transmits a sequence of RF pulses on the strip to produce a sensor field along the strip. A receiver is coupled to the second end of the strip, and generates a field reference signal in response to the sequence of pulse on the line combined with received electromagnetic energy from reflections in the field. The sensor signals comprise pulses of radio frequency signals having a duration of less than 10 nanoseconds, and a pulse repetition rate on the order of 1 to 10 MegaHertz or less. The duration of the radio frequency pulses is adjusted to control the range of the sensor. An RF detector feeds a filter capacitor in response to received pulses on the strip line to produce a field reference signal representing the average amplitude of the received pulses. When a received pulse is mixed with a received echo, the mixing causes a fluctuation in the amplitude of the field reference signal, providing a range-limited Doppler type signature of a field disturbance.

37 Claims, 3 Drawing Sheets

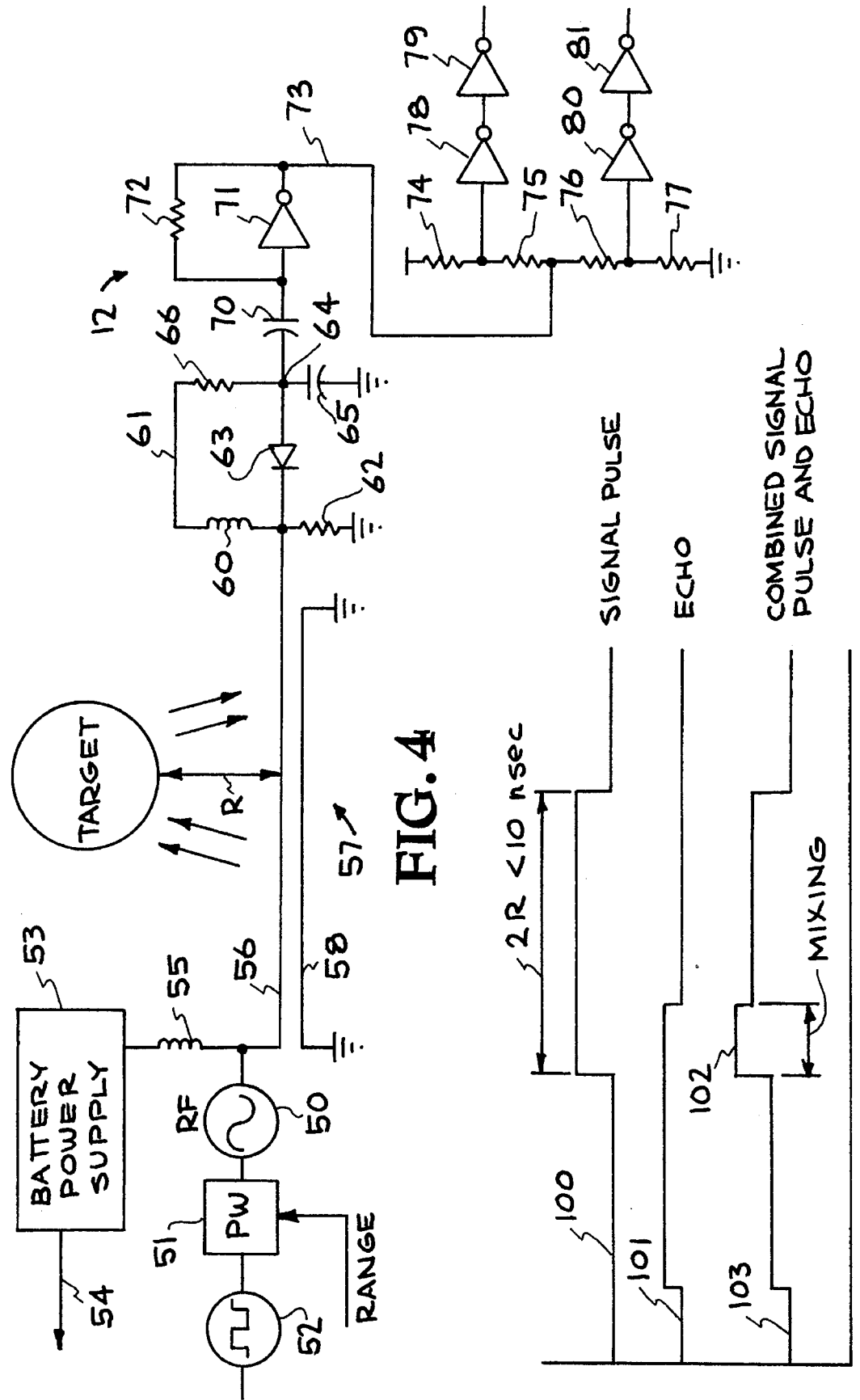

RANGE GATED STRIP PROXIMITY SENSOR

The U.S. Government has rights in this invention pursuant to Contract Number W-7405-ENG-48 between the U.S. Department of Energy and the University of California for the operation of Lawrence Livermore National Laboratory.

CONTINUING APPLICATION DATA

The present application is a continuation-in-part of my prior filed U.S. patent application entitled RANGE-GATED FIELD DISTURBANCE SENSOR WITH RANGE-SENSITIVITY COMPENSATION; Application No. 08/300,769; filed Sep. 6, 1994; now U.S. Pat. No. 5,521,600; issued May 28, 1996; invented by Thomas E. McEwan (IL-9514) which is incorporated by reference as if fully set forth herein.

BACKGROUND OF THE INVENTION

1. Field of the Invention

The present invention relates to short range proximity sensing along a narrow strip, and more particularly to short range strip proximity sensing using a single sensor based on micro-power impulse radar MIR.

2. Description of Related Art

Very short range proximity sensing according to the prior art requires a large number of sensors distributed at close intervals in order to provide continuous perimeter coverage. If the sensor's range is one foot, for example, sensors must be placed every two feet or closer to provide seamless coverage. For many applications, like detecting the perimeter of a large display case, or the perimeter of a car, a large number of sensors would be needed.

For example, in the parent U.S. patent application entitled RANGE-GATED FIELD DISTURBANCE SENSOR WITH RANGE-SENSITIVITY COMPENSATION (IL-9514); filed Sep. 6, 1994; application number 08/300,769; now U.S. Pat. No. 5,521,600; issued May 28, 1996; a micro-power impulse radar field disturbance sensor is described. However, a number of these sensors would be required to cover a long strip or the perimeter of a large object. Similarly, other prior art sensors, such as that described in Orlowski, et al., U.S. Pat. No. 5,150,123 are suitable for detecting disturbances only in relatively small fields. Thus, in order to monitor a large perimeter, expensive security systems are required based on large numbers of sensors, or other long range sensing technologies.

Accordingly, it is desirable to provide a low cost, effective, short range proximity sensing device which is capable of use along a long line or around a large perimeter.

SUMMARY OF THE INVENTION

The present invention provides a range gated strip proximity sensor using one set of sensor electronics and a distributed antenna or strip which extends along the perimeter to be sensed. In this way, a single strip can be meandered around a display case or around a car, coupled with a single set of low cost sensor electronics which detect motion or presence within a sharply bounded radial region around the strip. The strip may be made of a transmission line which is straight or contoured, and may be arbitrarily long. A user adjustable maximum detection range is continuously adjustable from near 0 to several tens of feet. The invention is particularly suitable for low cost volume applications, such as automotive parking assistance and home security.

Thus, the present invention can be characterized as a micro-power, strip line sensor which comprises a conductive line having a first end and a second end, and which acts as an antenna to produce electromagnetic emissions along the conductive line in response to signals on the conductive line, and to receive electromagnetic energy from sources outside the conductive line. A transmitter is coupled to the first end of the conductive line and transmits a sequence of sensor signals on the conductive line to produce a sensor field in a strip along the conductive line. A receiver is coupled to the second end of the conductive line, and generates a field reference signal in response to the sequence of sensor signals on the line combined with received electromagnetic energy from reflections in the field. Circuitry is coupled with the receiver and responds to the field reference signal to indicate disturbances in the field.

According to one aspect of the invention, the sensor signals comprise pulses of radio frequency signals having a duration of less than 10 nanoseconds, and a pulse repetition rate on the order of 1 to 10 MegaHertz or less. The duration of the radio frequency pulses is adjusted to control the range of the sensor. A mixer in the receiver mixes a transmitted pulse with reflections of the electromagnetic emissions caused by the burst to produce the field reference signal. Because of this homodyne mixing, the round-trip time of flight of the echoes is limited by the pulse width. Objects spaced farther away from the transmission line than a radius equal to the propagation speed of the pulse times one half the pulse width, will not result in homodyne mixing, and thus not be detected.

According to one aspect of the invention, the transmitter modulates the transmitted bursts at an intermediate frequency, and a circuit is coupled to the receiver which synchronously rectifies the samples at the intermediate frequency to provide signal gain and noise immunity.

According to another aspect of the invention, a circuit is coupled with the transmitter for adjusting the pulse width, so that the user may set the range of the strip proximity sensor.

The "leaky" transmission line can be arranged in a loop, such that the first and second ends are near one another, and the transmitter and receiver electronics placed nearby one another, or contained in a single package. Alternatively, the transmission line may extend essentially straight across a passageway, such as a doorway or the like. In this configuration, the transmission line can be used to carry DC power from the transmitter to the receiver, or vice versa.

The transmission line utilized may be twin lead, microstrip, coplanar strip or wave guide, or a single wire Gaobau line. Also, the transmission line may comprise a twisted pair of lines, with radiating elements spaced periodically along the twisted pair to establish the "leaky" condition.

According to another aspect of the invention, the receiver includes a sample gate and charge holding capacitor coupled to the sample gate. The sample gate feeds the charge holding capacitor in response to received pulses on the transmission line to produce a field reference signal representing the average amplitude of the received pulses. When a received pulse is mixed with a received echo, the mixing causes a fluctuation in the amplitude of the field reference signal, providing a Doppler type signature of a field disturbance.

Accordingly, a low cost strip proximity sensor is provided, with an adjustable and well defined range. The sensor is excellent for most short range sensing applications, such as parking assistance radar, automatic door safety strips, and security alarms. The strip can be meandered around display cases or automobiles to sense activity around the perimeter of an object. Alternatively, it can be used as a trip line across a passage way. The sensor uses a very low power and is simple to build.

Other aspects and advantages of the present invention can be seen upon review of the figures, the detailed description, and the claims which follow.

BRIEF DESCRIPTION OF THE FIGURES

FIG. 3 illustrates use of the present invention, laid out as a proximity sensor around the perimeter of an object, such as a display case or the like.

FIG. 4 is a schematic diagram of a strip proximity sensor electronics according to the present invention.

FIG. 5 is a timing diagram used to illustrate operation of the circuit of FIG. 4.

DETAILED DESCRIPTION

Figure 1:
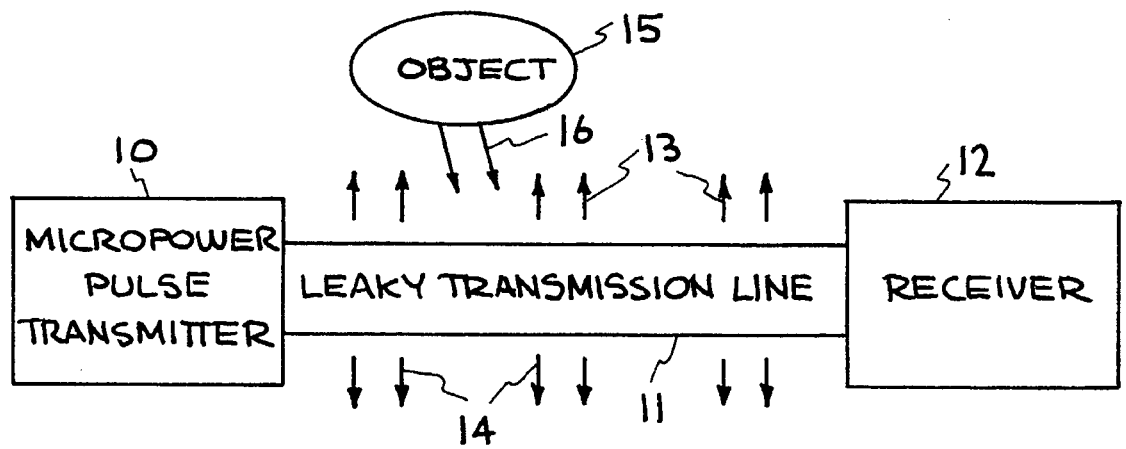
FIG. 1 is a schematic diagram illustrating the present invention using a leaky transmission line as the strip radiator.
Figure 2:
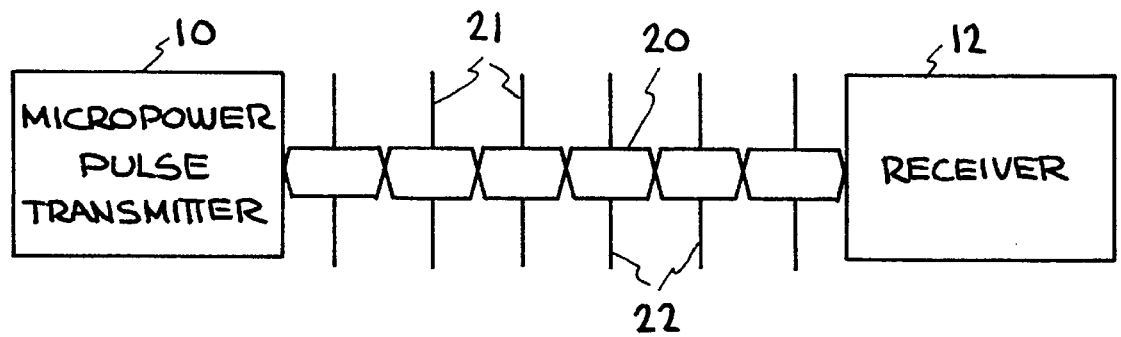
FIG. 2 is a schematic diagram showing use of a twisted pair transmission line with periodic radiating elements spaced along the transmission line.
Figure 3:
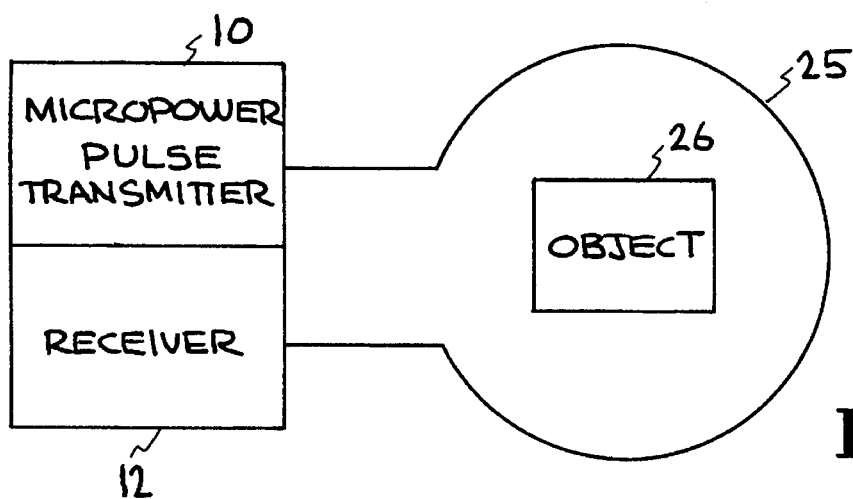
Figure 6:
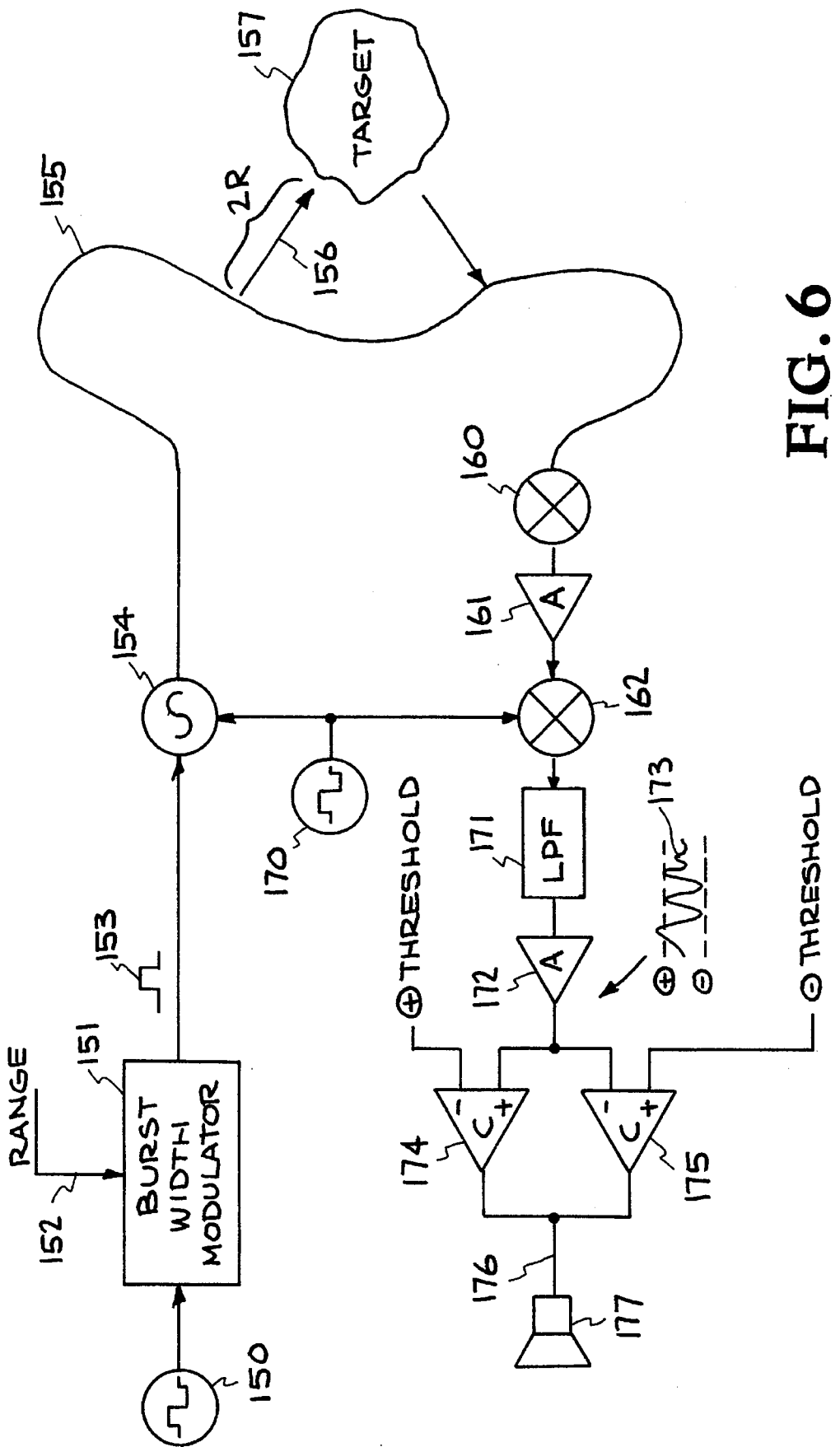
FIG. 6 is a schematic block diagram of an alternative implementation of the present invention.

A detailed description of preferred embodiments of the present invention is provided with reference to the figures, in which FIGS. 1 through 3 illustrate the basic configuration of the strip proximity sensor of the present invention. FIGS. 4 through 6 are used to illustrate two alternative embodiments of the strip proximity sensor electronics of the present invention.

Thus, as can be seen in FIG. 1, the strip proximity sensor of the present invention includes a micro-power pulse transmitter 10 coupled to a leaky transmission line 11. A receiver 12 is coupled to the opposite end of the leaky transmission line 11. The leaky transmission line 11 includes a conductor which carries a sequence of pulses generated by the micro-power pulse transmitter 10 from the first end of the transmission line to the second end of the transmission line. The pulses comprise a burst of radio frequency energy which causes emissions generally 13 and 14 along the length of the transmission line. In one embodiment, the RF burst is adjustable from 1 to 20 RF cycles at 2 GigaHertz. Objects, such as object 15, in the field result in reflections generally 16 which are picked up by the leaky transmission line. The receiver samples the pulses to generate a field reference signal. When the reflections 16 from the object 15 in the field mix with the transmitted pulses, then the amplitude of the received pulses fluctuates. This fluctuation results in a fluctuation of the field reference signal in the receiver indicating a disturbance along the strip defined by the leaky transmission line. The homodyne mixing action of the transmitted pulse and the received echoes depends on the round trip time of flight of the emissions from the transmission line and the reception of the echoes. As long as the round trip transmission time is less than the pulse width, homodyne mixing occurs in the signal propagating along the transmission line. This homodyne mixing creates fluctuations in the magnitude of the received pulse, which are interpreted as disturbances in the field. If the echoes do not overlap with the transmitted pulse, then insufficient effect on the field reference signal is caused by received echoes.

Because the transmitted pulses are less than about 10 nanoseconds long, repeated at a pulse repetition rate of 1 to 10 MegaHertz, the duty cycle of the micro-power pulse transmitter is very low. This results in very low power consumption for the device allowing long operational life using low cost batteries. The leaky transmission line 11 may be implemented using a twisted pair twin lead transmission line, a co-axial cable, a micro-strip transmission line, a coplanar strip or wave guide transmission line, or a single wire Gaobau line. The transmission line must be sufficiently leaky to allow radiation of emissions generated by the pulses, and reception of the echoes of such emissions.

FIG. 2 illustrates an alterative configuration for the leaky transmission line. As in FIG. 1, the system includes a micro-power pulse transmitter 10 and a receiver 12. The transmission line is implemented using a twisted pair transmission line 20. Periodically positioned along the twisted pair 20 are radiating elements 21, 22. These radiating elements cause the "leakage" of emissions in response to the transmitted pulses, and allow for reception of echoes. The radiators 21, 22 may be positioned in a pattern along the transmission line to control the regions in which strip proximity sensing is desired.

The strip sensor using a transmission line with periodic radiators is preferred for non-near field applications. A twisted transmission line eliminates spurious radiation from the transmission line itself and confines radiation emitted in response to the transmitted pulses to the periodic radiating elements. This system better defines the maximum operating range, by eliminating the spurious bi-static mode that appears in the system of FIG. 1 caused by reflections of emissions originating near the beginning of the transmission line that are received near the receiving end of the transmission line. These bi-static signals may cause fluctuations in the field reference signal from more distant objects. Bi-static mode is different from the direct local radiation mode in which a signal is transmitted from the transmission line directly to the target and back with a short round trip time of flight, and induces homodyne mixing. Thus, the use of periodic radiators may be desired for longer range applications.

FIG. 3 illustrates configuration of the present invention as a loop sensor. In this configuration, the micro-power pulse transmitter 10 and receiver 12 are positioned near one another. For instance, the electronics for the transmitter and receiver may be packaged in a single case, with suitable shielding. The transmission line 25 in FIG. 3 is configured in a loop around an object 26, such as a display case, an automobile, or the like. By positioning the transmitter and receiver close together, a single power supply may be utilized. Also, the timing of signals used in some embodiments of the transmitter and receiver may be simplified by the short signal propagation distances required.

The transmitter and receiver electronics may be implemented generally as described in the above cross-referenced application entitled RANGE GATED FIELD DISTURBANCE SENSOR WITH RANGE SENSITIVITY COMPENSATION, referred to above. Such application is incorporated by reference as if fully set forth herein for the purposes of teaching such electronics.

FIG. 4 illustrates one embodiment of the strip proximity sensor according to the present invention. The transmitter generally 10 includes a gated radio frequency oscillator 50. The gated radio frequency oscillator 50 is controlled by a pulse width control circuit 51. A pulse repetition rate for the system is controlled by a pulse repetition frequency square wave generator 52. The pulse repetition frequency is in the range of 1 to 10 MegaHertz. The radio frequency oscillator generates a short burst in the range of 1 to 10 GigaHertz. The pulse width modulator 51 has a controllable pulse width ranging from near zero to about 10 nanoseconds or longer.

A battery power supply 53 supplies power to the transmitter electronics as indicated by arrow 54. Also, the battery power supply is coupled through inductor 55 to a conductive line 56 in a two wire transmission line 57. Likewise, the gated radio frequency oscillator 50 supplies the RF pulse on the line 56. The second wire 58 in the two wire transmission line 57 is coupled to ground.

The receiver electronics generally 12 are coupled to the wire 56. An inductor 60 couples the DC power to a power line 61 on the receiver. This power line supplies the DC power for the electronics. The sampling circuitry in the receiver includes a resistor 62 coupled from line 56 to ground. A diode 63 which serves as a homodyne RF detector having its cathode coupled to wire 56 and its anode coupled to node 64. A filter capacitor 65 is coupled from node 64 to ground. Also a resistor 66 is coupled from node 64 to the power supply line 61. Node 64 is AC coupled through capacitor 70 to inverter 71 which is biased in the linear region. Inverter 71 has a resistor 72 coupled in feed back and drives line 73. Line 73 is coupled to the circuitry for detecting fluctuations in the signal on line 73, which is based on series resistors 74, 75, 76, and 77. Line 73 is coupled between resistors 75 and 76. Between resistors 74 and 75, a series of inverters 78 and 79 is connected. Similarly, between resistors 76 and 77, a series of inverters 80 and 81 is connected. The output of the amplifiers 79 and 81 can be compared to indicate disturbances in the field indicated by fluctuations in the field reference signal at node 64 held by the filter capacitor 65.

FIG. 5 illustrates the timing of the transmitted pulses, and is referred to in describing the operation of the receiver circuit 12 of FIG. 4. Trace 100 illustrates a time interval for a signal pulse as it is received at the receiver 12. Trace 101 illustrates a time interval for an echo of the signal pulse on trace 100, which follows the signal pulse by an amount of time less than the pulse width of the signal pulse. Trace 103 in FIG. 5 represents amplitude of a combined signal pulse and echo such as will be mixed by the detector 63 and filter capacitor 65 in the receiver electronics.

The signal pulses are transmitted along the transmission line having a length set by the pulse width modulator 51 of about 2R, or twice the radius R of the sensitive zone or cylinder around the transmission line. Thus, the length of the transmitted pulses as indicated by trace 100 in FIG. 5 is about 2R and typically less than about 10 nanoseconds. Echoes received off a target will arrive later than the signal pulse, as indicated along trace 101. To the extent that the echo on trace 101 overlaps with the pulse on trace 100, mixing occurs as indicated in the region 102 of trace 103.

The action of the detector 63 is to mix the signals which causes signal mixing as shown in the region 102 of trace 103. Signal mixing causes an increase in amplitude of the fluctuations sampled on the line, which when averaged over a large number of transmitted pulses causes the field reference signal on node 64 to fluctuate when a target object in the field moves or enters the field. Fluctuations are detected and amplified by the circuitry of FIG. 4 to indicate disturbances in the field.

The circuit of FIG. 4 is based on a two wire transmission line which carries power from the battery power supply 53 at the transmitter across the transmission line to the receiver electronics. An alternative in systems, a battery may be used in the receiver with transmission of power to the transmitter, a battery can be placed in each of the transmitter and the receiver, or other power supply distribution techniques may be utilized.

FIG. 6 is a block diagram of an alterative embodiment using a synchronous rectifier in the receiver to improve gain in the receiver and provide some noise immunity. Thus, a pulse repetition frequency oscillator 150 drives a burst width modulator 151 with a controlled range, as indicated by the signal on line 152. This results in gate pulse 153 having an adjustable width for gating a gated radio frequency oscillator 154. The radio frequency oscillator 154 drives the sequence of pulses on the transmission line 155 which emits radiation 156 into the field. Reflections off of a target 157 in the field are picked up by the transmission line 155. The combined signals on the transmission line 155 including the transmitted pulses and the received echoes are sampled in a radio frequency mixer 160 in the receiver. The mixer drives an intermediate frequency amplifier 161. The output of the intermediate frequency amplifier is supplied to a synchronous rectifier 162.

The gated RF oscillator 154 in the transmitter is amplitude modulated using an AM modulation oscillator 170. This AM oscillator turns on and off the gated RF oscillator 154 at approximately 10 kilohertz. The same 10 kilohertz AM modulation signal is supplied to the synchronous rectifier 162 in the receiver, which provides gain in the received signal and noise immunity.

The output of the synchronous rectifier 162 is supplied through a low pass filter 171 which drives a base band amplifier 172. The output of the amplifier 172 is a range-limited Doppler type signal 173 which indicates disturbances in the field around the transmission line 155. This signal at the output of amplifier 172 is supplied through a peak detector comprised of comparator 174 and comparator 175. The minus input of comparator 174 is supplied to a positive threshold. The positive input of comparator 174 is coupled to the output of amplifier 172. The output of amplifier 172 is supplied to the minus input of comparator 175. The positive input of comparator 175 is supplied to a negative threshold. The output of the comparators 174 and 175 are coupled together at node 176 and drive an alarm circuit 177.

Thus, according to the present invention a pulsed RF oscillator is used to drive a gated RF pulse down a leaky transmission line. The pulse repetition frequency is typically several MegaHertz. The pulse duration sets a limit on the two way time of flight to the target and, thus the radius of the sensor field along the strip. At the far end of the transmission line is an RF detector circuit, a high gain AC coupled amplifier for amplifying the Doppler signature of moving targets, and a threshold detector for triggering an alarm. The detector itself mixes the RF pulse carded on the transmission line with the reflected signal from the target to produce the Doppler signal that typically has a 0.1 to 10 Hertz frequency range for targets moving at human speeds.

For very short ranges from the transmission line, nearby or contacting objects produce a large impedance change in the line that can be sensed at the detector as a fluctuation in the received direct pulse amplitude. The sensing is not time resolved, and disturbances are sensed on the basis of amplitude only in the elemental embodiment of the sensor described herein. Range gating remains in effect by the virtue of the self mixing aspect of the received pulse with the echoes of the same pulse. Very close ranges can be accomplished using this impedance change sensing, along with short transmitted pulses.

In alternative systems, the electronics can be implemented using the techniques described in U.S. Pat. No. 5,345,471, entitled ULTRA-WIDE BAND RADAR MOTION SENSOR, (IL-9092). In this system, a timing link is connected from the transmit module to the receive module to cause the receive module to sample the RF pulse at an instant which corresponds to the desired time of flight to the target and back. The transmission line forms a loop, for instance around a display case, the transmit module and the receive module become one assembly and the timing link becomes local and quite practical.

Accordingly, the present invention provides a range gated strip proximity sensor which detects motion or presence within a well bounded radial region surrounding a transmission line. The transmission line may be straight or contoured, and may be arbitrarily long without re-timing for each length. The user adjustable maximum detection range is continuously adjustable from near zero to several tens of feet. The sensor is based on wide band, micro-power impulse radar sensing techniques and is intended for low cost volume applications, such as automotive parking assistance and home security. One configuration for automotive use places the leaky transmission line in a decorative strip surrounding the car that senses proximity to nearby objects for parking assistance, pre-collision sensing, security alarms, and keyless entry systems. Home and commercial applications include perimeter protection of small areas such as under window sills and around jewelry displays. Other uses include distributed respiration monitoring and robotic guidance systems.

The foregoing description of preferred embodiments of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A sensor comprising:
   a conductive line having a first end and a second end, which acts as an antenna to produce electromagnetic emissions along the conductive line in response to signals on the conductive line, and to receive electromagnetic energy from sources outside the conductive line;
   a transmitter coupled to the first end of the conductive line, which transmits a sequence of sensor signals on the conductive line to produce a sensor field of electromagnetic emissions along the conductive line, the sensor signals having a duration of less than about 10 nanoseconds;
   a receiver coupled to the second end of the conductive line which generates a field reference signal in response to the sequence of sensor signals and received electromagnetic energy on the conductive line; and
   circuitry, coupled to the receiver and responsive to the field reference signal, to indicate disturbances in the sensor field.

2. The sensor of claim 1, wherein the sequence of sensor signals comprises a sequence of transmitted radio frequency (RF) bursts, each RF burst having a burst width and comprising a number of cycles at a transmitter frequency; and wherein the receiver comprises:
   a mixer which mixes a transmitted RF burst with reflections of the emissions caused by the transmitted RF burst on the conductive line to produce the field reference signal.

3. The sensor of claim 2, including a circuit coupled to the transmitter which modulates the sequence of transmitted RF bursts at an intermediate frequency, and a circuit coupled to the receiver which synchronously rectifies the samples at the intermediate frequency.

4. The sensor of claim 2, including a circuit coupled to the transmitter by which to adjust the burst width of the RF bursts.

5. The sensor of claim 1, wherein the transmitter frequency is greater than one GigaHertz and the signal repetition rate is between 1 and 10 MegaHertz.

6. The sensor of claim 1, wherein the conductive line comprises a loop such that the first and second ends are near one another.

7. The sensor of claim 1, wherein the conductive line comprises a line extending essentially straight across a passageway.

8. The sensor of claim 1, wherein the conductive line comprises a line extending essentially along a perimeter.

9. The sensor of claim 1, wherein the conductive line comprises a leaky transmission line such that signals propagating along the line generate an essentially continuous sensor field.

10. The sensor of claim 1, wherein the conductive line comprises a
    plurality of radiating elements coupled to the conductive line in spaced apart positions between the first and second ends.

11. The sensor of claim 1, wherein the conductive line comprises a transmission line which carries DC power in addition to the sensor signals.

12. The sensor of claim 11, including a source of DC power on the transmitter coupled to the transmission line, and supplying DC power for the receiver across the transmission line.

13. The sensor of claim 1, wherein the sequence of radiated sensor signals has average power of less than 1 microWatt.

14. A sensor comprising:
    a conductive line having a first end and a second end, which acts as an antenna to produce electromagnetic emissions along the conductive line in response to signals on the conductive line, and to receive electromagnetic energy from sources outside the conductive line;
    a transmitter coupled to the first end of the conductive line, which transmits a sequence of radio frequency (RF) pulses on the conductive line to produce a sensor field of electromagnetic emissions along the conductive line, the RF pulses having a duration of less than about 10 nanoseconds;
    a receiver coupled to the second end of the conductive line, including a mixing detector and a filter capacitor coupled to the detector which produce a field reference signal representing amplitude of RF pulses received at the second end of the conductive line;
    circuitry, coupled to the receiver and responsive to the field reference signal, to indicate disturbances in the sensor field.

15. The sensor of claim 14, including a circuit coupled to the transmitter which amplitude modulates the sequence of RF pulses at an intermediate frequency, and a circuit coupled to the receiver which synchronously rectifies the field reference signal at the intermediate frequency.

16. The sensor of claim 14, wherein the sequence of RF pulses comprise transmitted bursts having a nominal frequency of greater than about 1 GigaHertz, and a pulse repetition rate of less than about 10 MegaHertz.

17. The sensor of claim 16, including a circuit coupled to the transmitter by which to adjust the duration of the RF pulses.

18. The sensor of claim 14, wherein the conductive line comprises a loop such that the first and second ends are near one another.

19. The sensor of claim 14, wherein the conductive line comprises a line extending essentially straight across a passageway.

20. The sensor of claim 14, wherein the conductive line comprises a line extending essentially along a perimeter.

21. The sensor of claim 14, wherein the conductive line comprises a leaky transmission line such that signals propagating along the line generate an essentially continuous sensor field.

22. The sensor of claim 14, wherein the conductive line comprises a
  plurality of radiating elements coupled to the conductive line in spaced apart positions between the first and second ends.

23. The sensor of claim 14, wherein the conductive line comprises a transmission line which carries DC power in addition to the sensor signals.

24. The sensor of claim 23, including a source of DC power on the transmitter coupled to the transmission line, and supplying DC power for the receiver across the transmission line.

25. A micropower strip proximity sensor comprising:
  a conductive line having a first end and a second end, which acts as an antenna to produce electromagnetic emissions along the conductive line in response to signals on the conductive line, and to receive electromagnetic energy from sources outside the conductive line;
  a transmitter coupled to the first end of the conductive line, which transmits a sequence of radio frequency (RF) pulses on the conductive line to produce a sensor field of electromagnetic emissions in a strip along the conductive line, the sequence of signals having a signal repetition rate and pulse width so that average radiated power of the transmitter is less than about 1 microWatt;
  a receiver coupled to the second end of the conductive line, including a mixing detector and a filter capacitor coupled to the detector which produce a field reference signal representing an average amplitude of signals received at the second end of the conductive line;
  circuitry, coupled to the receiver and responsive to the field reference signal, to indicate disturbances in the sensor field.

26. The sensor of claim 25, including a circuit coupled to the transmitter which amplitude modulates the sequence of RF pulses at an intermediate frequency, and a circuit coupled to the receiver which synchronously rectifies the field reference signal at the intermediate frequency.

27. The sensor of claim 25, wherein the sequence of RF pulses comprise transmitted bursts having a nominal frequency of greater than about 1 GigaHertz and a duration of less than about 10 nanoseconds, and a pulse repetition rate of less than about 10 MegaHertz.

28. The sensor of claim 27, including a circuit coupled to the transmitter by which to adjust the duration of the RF pulses.

29. The sensor of claim 25, wherein the sensor field has a width along the conductive line, and including a circuit coupled to the transmitter by which to adjust the width of the sensor field along the conductive line.

30. The sensor of claim 29, wherein the circuit adjusts the width of the sensor field by adjusting the duration of the RF pulses.

31. The sensor of claim 25, wherein the conductive line comprises a loop such that the first and second ends are near one another.

32. The sensor of claim 25, wherein the conductive line comprises a line extending essentially straight across a passageway.

33. The sensor of claim 25, wherein the conductive line comprises a line extending essentially along a perimeter.

34. The sensor of claim 25, wherein the conductive line comprises a leaky transmission line such that signals propagating along the line generate an essentially continuous sensor field.

35. The sensor of claim 25, wherein the conductive line comprises a plurality of radiating elements coupled to the conductive line in spaced apart positions between the first and second ends.

36. The sensor of claim 25, wherein the conductive line comprises a transmission line which carries DC power in addition to the sensor signals.

37. The sensor of claim 36, including a source of DC power on the transmitter coupled to the transmission line, and supplying DC power for the receiver across the transmission line.

* * * * *